United States Patent
Leuridan et al.

(12)

(10) Patent No.: US 6,372,201 B1
(45) Date of Patent: Apr. 16, 2002

(54) NAIL VARNISH COMPRISING AN AQUEOUS POLYMER DISPERSION

(75) Inventors: Frédéric Leuridan, Paris; Dolores Colombel, L'Hay-les-Roses; Bertrand Lion, Livry Gargan, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/539,422

(22) Filed: Mar. 30, 2000

(30) Foreign Application Priority Data

Apr. 1, 1999 (FR) .................................. 99 04103

(51) Int. Cl.$^7$ .................... A61K 7/04; A61K 7/025; A61K 9/14; A61K 9/16
(52) U.S. Cl. .................... 424/61; 424/64; 424/489; 424/497
(58) Field of Search .................... 424/61, 64, 497, 424/489

(56) References Cited

U.S. PATENT DOCUMENTS

| | | | | | |
|---|---|---|---|---|---|
| 4,158,053 | A | * | 6/1979 | Greene et al. | 424/61 |
| 5,120,529 | A | | 6/1992 | Koch et al. | 424/61 |
| 5,607,665 | A | | 3/1997 | Calello et al. | 424/61 |
| 5,639,447 | A | | 6/1997 | Patel | 424/61 |
| 5,688,493 | A | | 11/1997 | Sugawara et al. | 424/61 |
| 5,961,989 | A | | 10/1999 | Mougin et al. | 424/401 |

FOREIGN PATENT DOCUMENTS

| | | |
|---|---|---|
| EP | 0 424 112 | 4/1991 |
| EP | 0 815 848 | 1/1998 |
| FR | 2 221 503 | 10/1974 |
| FR | 2 733 147 | 10/1996 |
| FR | 2 739 022 | 3/1997 |
| GB | 1465190 | 2/1977 |
| JP | 4-103513 | 4/1992 |
| JP | 4-297408 | 10/1992 |
| JP | 4-297409 | 10/1992 |
| JP | 5-39210 | 2/1993 |
| JP | 7-309721 | 11/1995 |
| JP | 8-92038 | 4/1996 |
| JP | 9-71512 | 3/1997 |
| WO | WO 97/00664 | 1/1997 |

OTHER PUBLICATIONS

Allan F.M. Barton, Ph.D., "CRC Handbook of Solubility Parameters and Other Cohesion Parameters", Second Edition, 1991, pp. 95–109.

Charles M. Hansen, "The Three Dimensional Solubility Parameter—Key to Paint Component Affinities: I. Solvents, Plasticizers, Polymers, and Resins", Journal of Paint Technology, vol. 39, No. 505, Feb. 1967, pp. 104–117.

A. Toussaint et al., "A Method to Predict the Distribution Coefficient of Coalescing Agents Between Latex Particles and the Water Phase", Progress in Organic Coatings, vol. 30, No. 3, Mar. 1997, pp. 173–177.

Patent Abstracts of Japan, vol. 1998, No. 06, Apr. 30, 1998 (JP 10 036227).

Patent Abstracts of Japan, vol. 1995, No. 07, Aug. 31, 1995 (JP 07 089827).

English language Derwent Abstract of EP 0 815 848, Jan. 1998.

English language Derwent Abstract of FR 2 221 503, Oct. 1974.

English language Derwent Abstract of FR 2 733 147, Oct. 1996.

English language Derwent Abstract of JP 4–103513, Apr. 1992.

English language Derwent Abstract of JP 4–297408, Oct. 1992.

English language Derwent Abstract of JP 4–297409, Oct. 1992.

English language Derwent Abstract of JP 5–39210, Feb. 1993.

English language Derwent Abstract of JP 7–309721, Nov. 1995.

English language Derwent Abstract of JP 8–92038, Apr. 1996.

English language Derwent Abstract of JP 9–71512, Mar. 1997.

* cited by examiner

Primary Examiner—Thurman K. Page
Assistant Examiner—Rachel M. Bennett
(74) Attorney, Agent, or Firm—Finnegan, Henderson, Farabow, Garrett & Dunner, L.L.P.

(57) ABSTRACT

A nail varnish or nailcare composition containing an aqueous dispersion of particles of acrylic polymer having a glass transition temperature (Tg) greater than or equal to 45° C. and a minimum film-forming temperature (MFT) such that Tg−MFT≦20° C., a first organic solvent having a boiling point measured at ambient pressure of greater than or equal to 225° C. and a second organic solvent having a boiling point measured at ambient pressure ranging from 70° C. to 180° C. A method of making up and/or caring for the nails which includes applying the composition to the nails. The nail composition is adherent to the nail, is bright and is easily removed with conventional removers.

26 Claims, No Drawings

NAIL VARNISH COMPRISING AN AQUEOUS POLYMER DISPERSION

This application claims priority to FRANCE 9904103 filed Apr. 1, 1999.

The present invention relates to a nail varnish or nailcare composition comprising an aqueous dispersion of polymer particles, a plasticizer and a coalescent. The invention also relates to a method of making up and/or caring for the nails, especially human nails or false nails.

The nail varnish or nailcare composition can be employed as a varnish base, as a nail makeup product, as a finishing composition, also referred to as a "topcoat", for application over a nail makeup product, or else as a cosmetic nailcare product.

Nail varnish compositions are known which comprise aqueous dispersions of particles of a film-forming polymer. The properties of these varnishes are not always satisfactory. In particular, the film may exhibit poor adhesion to the nail and/or may not be sufficiently bright. Moreover, the varnish, after drying, is often difficult to remove, even with the conventional removers based on acetone or ethyl acetate, for example.

An object of the present invention is to provide an aqueous nail varnish medium exhibiting good properties such as adhesion to the nail and brightness and also removability with the conventional removers based on acetate and/or ethyl acetate.

The inventors have found that such a nail varnish can be obtained by employing an aqueous dispersion of polymer particles in combination with selected solvents.

The invention provides a nail varnish or nailcare composition comprising an aqueous dispersion of polymer particles, wherein:

the polymer is an acrylic polymer having at least one glass transition temperature (Tg) greater than or equal to 45° C. and a minimum film-forming temperature (MFT) such that $$Tg-MFT \leq 20° C.,$$

and wherein the composition further comprises:
at least one first organic solvent having a boiling point measured at ambient pressure of greater than or equal to 225° C., and
at least one second organic solvent having a boiling point measured at ambient pressure ranging from 70° C. to 180° C.

The invention additionally provides a cosmetic makeup and/or nailcare method which comprises applying a composition as defined above to the nails.

The invention further provides for the use, in a nail varnish or nailcare composition, of an acrylic polymer in aqueous dispersion having at least one glass transition temperature (Tg) greater than or equal to 45° C. and a minimum film-forming temperature (MFT) such that Tg–MFT≦20° C., of a first organic solvent having a boiling point measured at ambient pressure of greater than or equal to 225° C., and of a second organic solvent having a boiling point measured at ambient pressure ranging from 70° C. to 180° C., to obtain a film which is removable with acetone and/or with ethyl acetate and/or which is adherent to the nail and/or bright.

Advantageously, the acrylic polymer has at least one glass transition temperature (Tg) greater than or equal to 45° C. and a minimum film-forming temperature (MFT) such that Tg–MFT≦10° C., and more preferably ≦5° C.

Preferably, the polymer in aqueous dispersion has a glass transition temperature Tg of less than 70° C. and more preferably of from 55° C. to 65° C. The glass transition temperature (Tg) is measured by DSC (Differential Scanning Calorimetry) in accordance with the standard ASTM D3418-97.

The acrylic polymer can be a styrene/acrylate copolymer and, in particular, a polymer selected from copolymers obtained by polymerizing at least one styrene monomer and at least one ($C_1$–$C_{18}$) alkyl (meth)acrylate monomer.

As a styrene monomer which can be used in the invention, mention may be made of styrene or alpha-methylstyrene, preferably styrene.

The ($C_1$–$C_{18}$) alkyl (meth)acrylate monomer is preferably a ($C_1$–$C_{12}$) alkyl (meth) acrylate and more preferably a ($C_1$–$C_{10}$) alkyl (meth)acrylate.

The ($C_1$–$C_{18}$) alkyl (meth)acrylate monomer is selected from methyl acrylate, methyl methacrylate, ethyl acrylate, propyl acrylate, butyl acrylate, butyl methacrylate, hexyl acrylate, octyl acrylate, 2-ethylhexyl acrylate, lauryl (meth)acrylate and stearyl (meth)acrylate.

Advantageously, the acrylic polymer in aqueous dispersion has solubility properties at 25° C. in organic solvents, corresponding to the average Hansen solubility parameters dD, dP and dH, which satisfy the following conditions:

dD=17.5
dP=7
dH=7.6 with a radius R ranging from 5 to 10, and preferably from 5 to 6.

The definition of the solvents in the three-dimensional solubility space according to Hansen is described in the article by C. M. Hansen: "The three dimensional solubility parameters", J. Paint Technol. 39, 105 (1967), the disclosure of which is specifically incorporated by reference herein.

dD characterizes the London dispersion forces resulting from the formation of dipoles induced on molecular impact.

dP characterizes the Debye interaction forces between permanent dipoles and the Keesom interaction forces between induced dipoles and permanent dipoles.

dH characterizes the specific interaction forces (of the hydrogen bonding, acid/base, donor/acceptor type, etc.).

The parameters dD, dP and dH are expressed in $(J/Cm^3)^{1/2}$.

The radius R corresponds to the distance, in the Hansen solubility parameter space, separating an organic solvent from the point in the space corresponding to dD=17.5; dP=7; dH=7.6, R meeting the following condition:

$$5J^{-1/2}cm^{-3/2} \leq R \leq 10J^{1/2}cm^{-3/2},$$

in which:

$$R = \sqrt{4(\delta^s{}_d - 17.5)^2 + (\delta^s{}_p - 7)^2 + (\delta^s{}_h - 7.6)^2}$$

where $\delta^s{}_d$, $\delta^s{}_p$, $\delta^s{}_h$ are the Hansen solubility parameters of an organic solvent for which the acrylic polymer used in the present invention has solubility properties. The definition of the radius R is known from the work by Allan F. M. Barton, CRC Handbook of solubility parameters and other cohesion parameters, Second edition, 1991, pages 95 to 109, the disclosure of which is specifically incorporated by reference herein.

As the acrylic polymer in aqueous dispersion, use may be made in accordance with the invention of the styrene/acrylate copolymer marketed under the name JONCRYL SCX-8211 by the company Johnson.

In accordance with one particular embodiment of the invention, the composition may comprise as sole polymer in aqueous dispersion the acrylic polymer defined above.

The acrylic polymer in aqueous dispersion may be present in an amount, in terms of dry matter, which is effective for forming a film, preferably in an amount ranging from 3% to 50% by weight, relative to the total weight of the composition, and more preferably from 10% to 40% by weight.

The first organic solvent present in the composition, which is also called the plasticizer, makes it possible to plasticize the polymer in aqueous dispersion. Preferably, the first organic solvent can have a distribution coefficient D of less than or equal to 0.1. The distribution coefficient is determined in accordance with the teaching of "A method to predict the distribution coefficient of coalescing agents between latex particles and the water phase," *Progress in Organic Coatings*, vol. 30, 1997, pp. 173–177, the disclosure of which is specifically incorporated by reference herein.

The first organic solvent according to the invention is preferably selected from diisobutyl adipate, the ester of tertbutyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, and mixtures thereof.

Even more preferably, the first organic solvent may be selected from diisobutyl adipate, the ester of tertbutyl acid and 2,2,4-trimethylpentane-1,3-diol, dipropylene glycol n-butyl ether, and mixtures thereof.

Preferably, the first organic solvent has a boiling point measured at ambient pressure of less than or equal to 285° C., preferably less than or equal to 270° C. and, more preferably, less than or equal to 250° C. In the present specification, the boiling point values are to be considered accurate to ±2° C. owing to the uncertainties of boiling point measurement.

The first organic solvent can be present in the composition according to the invention in an amount preferably ranging from 0.1% to 20% by weight, relative to the total weight of the composition, and more preferably from 0.5% to 10%.

The second organic solvent present in the composition, which is also called the coalescent, promotes the coalescence of the polymer particles in aqueous dispersion. Preferably, the second organic solvent may have a distribution coefficient D' of greater than or equal to 0.5, measured in accordance with the above-referenced "A method to predict the distribution coefficient of coalescing agents between latex particles and the water phase," *Progress in Organic Coatings*, vol. 30, 1997, pp.173–177.

As the second organic solvent, use may be preferably made according to the invention of propylene glycol n-butyl ether, dipropylene glycol dimethyl ether, propylene glycol methyl ether acetate, propylene glycol propyl ether, methyl lactate, ethyl lactate, isopropyl lactate, and mixtures thereof.

More preferably, the second organic solvent is selected from propylene glycol n-butyl ether, dipropylene glycol dimethyl ether, isopropyl lactate, and mixtures thereof.

Preferably, the second organic solvent has a boiling point measured at ambient pressure ranging from 90° C. to 180° C., and more preferably from 150° C. to 180° C.

The second organic solvent may be present in the composition in an amount preferably ranging from 2% to 15% by weight, relative to the total weight of the composition, more preferably from 3% to 10%.

The composition of the invention may further comprise at least one additive chosen from thickeners, leveling agents, wetting agents, dispersants, antifoams, preservatives, UV screens, dyes, pigments, active principles, surfactants, moisturizers, perfumes, neutralizing agents, stabilizers, antioxidants, and combinations thereof.

The invention is illustrated in greater detail in the following examples:

EXAMPLE 1

A nail varnish was prepared having the following composition:

| | |
|---|---|
| acrylate-styrene polymer in aqueous dispersion containing 44% dry matter (JONCRYL SCX-8211 from the company Johnson) | 28.8 g a.s. (active substance) |
| diisobutyl adipate | 2.8 g |
| propylene glycol n-butyl ether | 2.7 g |
| dipropylene glycol n-butyl ether | 1.6 g |
| Laponite XLS | 0.8 g |
| pigments | 2 g |
| water   qsp | 100 g |

The varnish was easy to apply and led, after drying, to a bright film which adhered well to the nail and was able to be removed with acetone or ethyl acetate.

EXAMPLE 2

A nail varnish was prepared having the following composition:

| | |
|---|---|
| acrylate-styrene polymer in aqueous dispersion containing 44% dry matter (JONCRYL SCX-8211 from the company Johnson) | 30 g a.s. |
| ester of tertbutyl acid and 2,2,4-trimethylpentane-1,3-diol | 2.8 g |
| propylene glycol n-butyl ether | 2 g |
| dipropylene glycol n-butyl ether | 1.6 g |
| Laponite XLS | 0.8 g |
| pigments | 2 g |
| water   qsp | 100 g |

The varnish was easy to apply and led, after drying, to a bright film which adhered well to the nail and was able to be removed with acetone or ethyl acetate.

What is claimed is:

1. A nail varnish or nailcare composition comprising:
   an aqueous dispersion of polymer particles,
   at least one first organic solvent having a boiling point measured at ambient pressure of greater than or equal to 225° C., and
   at least one second organic solvent having a boiling point measured at ambient pressure ranging from 70° C. to 180° C.,
   wherein the aqueous dispersion of polymer particles comprises an acrylic polymer having at least one glass transition temperature (Tg) greater than or equal to 45° C. and a minimum film-forming temperature (MFT) such that Tg−MFT≦20° C.

2. The composition as claimed in claim 1, wherein the acrylic polymer has at least one glass transition temperature (Tg) greater than or equal to 45° C. and a minimum film-forming temperature (MFT) such that Tg−MFT≦10° C.

3. The composition as claimed in claim 2, wherein the acrylic polymer has at least one glass transition temperature (Tg) greater than or equal to 45° C. and a minimum film-forming temperature (MPT) such that Tg−MFT≦5° C.

4. The composition as claimed in claim 1, wherein the glass transition temperature (Tg) of the acrylic polymer is less than 70° C.

5. The composition as claimed in claim 1, wherein the glass transition temperature (Tg) of the acrylic polymer ranges from 55° C. to 65° C.

6. The composition as claimed in claim 1, wherein the acrylic polymer comprises a styrene/acrylate copolymer.

7. The composition as claimed in claim 6, wherein the styrene/acrylate copolymer comprises at least one ($C_1$–$C_{18}$) alkyl (meth)acrylate monomeric unit.

8. The composition as claimed in claim 6, wherein the styrene/acrylate copolymer comprises at least one ($C_1$–$C_{10}$) alkyl acrylate monomeric unit.

9. The composition as claimed in claim 1, wherein the aqueous dispersion of polymer particles consists essentially of the acrylic polymer.

10. The composition as claimed in claim 1, wherein the acrylic polymer is present, in terms of dry matter, in an amount ranging from 3% to 50% by weight relative to the total weight of the composition.

11. The composition as claimed in claim 10, wherein the acrylic polymer is present, in terms of dry matter, in an amount ranging from 10% to 40% by weight relative to the total weight of the composition.

12. The composition as claimed in claim 1, wherein the at least one first organic solvent has a boiling point measured at ambient pressure of greater than or equal to 230° C.

13. The composition as claimed in claim 1, wherein the at least one first organic solvent has a distribution coefficient D of less than or equal to 0.1.

14. The composition as claimed in claim 1, wherein the at least one first organic solvent is chosen from diisobutyl adipate, the ester of tertbutyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, and dipropylene glycol n-butyl ether.

15. The composition as claimed in claim 14, wherein the at least one first organic solvent is chosen from diisobutyl adipate, the ester of tertbutyl acid and 2,2,4-trimethylpentane-1,3-diol, and dipropylene glycol n-butyl ether.

16. The composition as claimed in claim 1, wherein the at least one first organic solvent is present in the composition in an amount ranging from 0.1% to 20% by weight relative to the total weight of the composition.

17. The composition as claimed in claim 16, wherein the at least one first organic solvent is present in the composition in an amount ranging from 0.5% to 10% by weight relative to the total weight of the composition.

18. The composition as claimed in claim 1, wherein the at least one second organic solvent has a distribution coefficient D' of greater than or equal to 0.5.

19. The composition as claimed in claim 1, wherein the at least one second organic solvent is chosen from propylene glycol n-butyl ether, dipropylene glycol dimethyl ether, propylene glycol methyl ether acetate, propylene glycol propyl ether, methyl lactate, ethyl lactate, and isopropyl lactate.

20. The composition as claimed in claim 19, wherein the at least one second organic solvent is chosen from propylene glycol n-butyl ether, dipropylene glycol dimethyl ether, and isopropyl lactate.

21. The composition as claimed in claim 1, wherein the at least one second organic solvent is present in the composition in an amount ranging from 2% to 15% by weight relative to the total weight of the composition.

22. The composition as claimed in claim 1, wherein the at least one second organic solvent is present in the composition in an amount ranging from 3% to 10% by weight relative to the total weight of the composition.

23. The composition as claimed in claim 1, further comprising at least one additive chosen from thickeners, leveling agents, wetting agents, dispersants, antifoams, preservatives, UV screens, dyes, pigments, active principles, surfactants, moisturizers, perfumes, neutralizing agents, stabilizers and antioxidants.

24. A method for making up and/or caring for nails comprising applying to the nails a composition comprising:
   an aqueous dispersion of polymer particles,
   at least one first organic solvent having a boiling point measured at ambient pressure of greater than or equal to 225° C., and
   at least one second organic solvent having a boiling point measured at ambient pressure ranging from 70° C. to 180° C.,
   wherein the aqueous dispersion of polymer particles comprises an acrylic polymer having at least one glass transition temperature (Tg) greater than or equal to 45° C. and a minimum film-forming temperature (MFT) such that Tg−MFT≦20° C.

25. A method of treating a nail to obtain a film which is removable with acetone and/or with ethyl acetate and/or which is adherent to the nail and/or bright comprising the step of applying to said nail an effective amount of a composition comprising:
   an aqueous dispersion of polymer particles,
   at least one first organic solvent having a boiling point measured at ambient pressure of greater than or equal to 225° C., and
   at least one second organic solvent having a boiling point measured at ambient pressure ranging from 70° C. to 180° C.,
   wherein the aqueous dispersion of polymer particles comprises an acrylic polymer having at least one glass transition temperature (Tg) greater than or equal to 45° C. and a minimum film-forming temperature (MFT) such that Tg−MFT≦20° C.

26. A composition according to claim 1, wherein said aqueous dispersion of polymer particles comprises an acrylic polymer in aqueous dispersion having solubility properties at 25° C. in an organic solvent, which satisfy the following conditions:
   dD=17.5
   dP=7
   dH=7.6
with a radius R ranging from 5 to 10.

* * * * *